(12) United States Patent
Rousseau

(10) Patent No.: US 9,326,886 B2
(45) Date of Patent: May 3, 2016

(54) FLUID FILLED IMPLANTS FOR TREATING OBSTRUCTIVE SLEEP APNEA

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 272 days.

(21) Appl. No.: 12/608,057

(22) Filed: Oct. 29, 2009

(65) Prior Publication Data

US 2011/0100376 A1 May 5, 2011

(51) Int. Cl.
*A61F 5/37* (2006.01)
*A61F 13/00* (2006.01)
*A61M 5/00* (2006.01)
*A61F 2/06* (2013.01)
*A61B 5/103* (2006.01)
(Continued)

(52) U.S. Cl.
CPC . *A61F 5/566* (2013.01); *A61B 5/00* (2013.01); *A61B 5/48* (2013.01); *A61B 5/4806* (2013.01); *A61B 5/4818* (2013.01); *A61F 5/00* (2013.01); *A61F 5/37* (2013.01); *A61F 5/56* (2013.01); *A61F 5/0013* (2013.01); *A61F 5/0033* (2013.01)

(58) Field of Classification Search
CPC ........... A61F 5/00; A61F 5/56; A61F 5/0013; A61F 5/003; A61F 5/0033; A61F 5/37; A61F 5/566; A61B 5/00; A61B 5/48; A61B 5/4806; A61B 5/4818
USPC .................. 128/846, 847, 848, 859; 602/902; 604/8–10; 623/1.14, 1.15, 1.17, 1.18, 623/1.2, 1.22, 1.25; 600/590, 593
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |

(Continued)

FOREIGN PATENT DOCUMENTS

| | | |
|---|---|---|
| CN | 2465680 | 12/2001 |
| CN | 201029957 | 3/2008 |

(Continued)

OTHER PUBLICATIONS

Friedman et al., A System and Method for Inserting a Medical Device for Treatment of Sleep Apnea via the Nasal Passage, and Device Therefor, Dec. 29, 2008, Provisional U.S. Appl. No. 61/203,758, p. 8 & p. 6/8.*

(Continued)

*Primary Examiner* — Alireza Nia
*Assistant Examiner* — Brandon L Jackson
(74) *Attorney, Agent, or Firm* — Doherty IP Law Group LLC

(57) ABSTRACT

An implant for treating obstructive sleep apnea includes a flexible chamber, a fluid reservoir in fluid communication with the flexible chamber, and a fluid transfer assembly in communication with the fluid reservoir and the flexible chamber for transferring fluid therebetween for selectively modifying the rigidity of the flexible chamber. The flexible chamber is implantable within the soft tissue of an oropharyngeal airway of a patient, such as within the tongue, the soft palate, or the pharyngeal wall. The fluid reservoir and the fluid transfer assembly are implantable within the inframandibular region of the patient. The fluid transfer assembly is selectively engageable by the patient for transferring fluid between the two chambers for modifying the rigidity, flexibility, and/or shape of the flexible chamber with minimal or no change to the volume of the implant.

24 Claims, 10 Drawing Sheets

(51) Int. Cl.
    *A61B 5/117*     (2006.01)
    *A61F 5/56*     (2006.01)
    *A61B 5/00*     (2006.01)
    *A61F 5/00*     (2006.01)

(56) References Cited

U.S. PATENT DOCUMENTS

| | | | |
|---|---|---|---|
| 4,069,825 | A | 1/1978 | Akiyama |
| 4,091,816 | A * | 5/1978 | Elam ............... 128/207.15 |
| 4,290,763 | A | 9/1981 | Hurst |
| 4,523,584 | A | 6/1985 | Yachia et al. |
| 4,557,264 | A | 12/1985 | Hinsch |
| 4,839,215 | A | 6/1989 | Starling et al. |
| 4,881,939 | A | 11/1989 | Newman |
| 4,950,285 | A | 8/1990 | Wilk |
| 5,053,047 | A | 10/1991 | Yoon |
| 5,067,485 | A | 11/1991 | Cowen |
| 5,123,913 | A | 6/1992 | Wilk et al. |
| 5,192,271 | A | 3/1993 | Kalb et al. |
| 5,192,274 | A | 3/1993 | Bierman |
| 5,269,783 | A | 12/1993 | Sander |
| 5,284,161 | A | 2/1994 | Karell |
| 5,311,028 | A | 5/1994 | Glavish |
| 5,393,984 | A | 2/1995 | Glavish |
| 5,483,077 | A | 1/1996 | Glavish |
| 5,484,444 | A | 1/1996 | Braunschweiler et al. |
| 5,609,559 | A | 3/1997 | Weitzner |
| 5,683,417 | A | 11/1997 | Cooper |
| 5,704,895 | A | 1/1998 | Scott et al. |
| 5,792,067 | A | 8/1998 | Karell |
| 5,843,077 | A | 12/1998 | Edwards |
| 5,931,855 | A | 8/1999 | Buncke |
| 6,048,851 | A | 4/2000 | Bernstein |
| 6,161,541 | A | 12/2000 | Woodson |
| 6,190,401 | B1 | 2/2001 | Green et al. |
| 6,241,747 | B1 | 6/2001 | Ruff |
| 6,250,307 | B1 | 6/2001 | Conrad et al. |
| 6,348,156 | B1 | 2/2002 | Vishnoi et al. |
| 6,431,174 | B1 | 8/2002 | Knudson et al. |
| 6,432,437 | B1 | 8/2002 | Hubbard |
| 6,457,472 | B1 | 10/2002 | Schwartz et al. |
| 6,513,530 | B2 | 2/2003 | Knudson et al. |
| 6,523,542 | B2 | 2/2003 | Knudson et al. |
| 6,578,580 | B2 | 6/2003 | Conrad et al. |
| 6,589,549 | B2 | 7/2003 | Shih et al. |
| 6,599,310 | B2 | 7/2003 | Leung et al. |
| 6,627,600 | B2 | 9/2003 | Boutignon |
| 6,634,362 | B2 | 10/2003 | Conrad et al. |
| 6,638,284 | B1 | 10/2003 | Rousseau et al. |
| 6,716,251 | B1 | 4/2004 | Asius et al. |
| 6,742,524 | B2 | 6/2004 | Knudson et al. |
| 6,755,868 | B2 | 6/2004 | Rousseau |
| 6,800,082 | B2 | 10/2004 | Rousseau |
| 6,899,105 | B2 | 5/2005 | Krueger et al. |
| 6,955,172 | B2 | 10/2005 | Nelson et al. |
| 6,981,944 | B2 | 1/2006 | Jamiolkowski et al. |
| 7,017,582 | B2 | 3/2006 | Metzger et al. |
| 7,056,331 | B2 | 6/2006 | Kaplan et al. |
| 7,135,189 | B2 | 11/2006 | Knapp |
| 7,146,981 | B2 | 12/2006 | Knudson et al. |
| 7,166,570 | B2 | 1/2007 | Hunter et al. |
| 7,213,599 | B2 | 5/2007 | Conrad et al. |
| 7,237,554 | B2 | 7/2007 | Conrad et al. |
| 7,261,702 | B1 | 8/2007 | Alexandre et al. |
| 7,288,075 | B2 | 10/2007 | Parihar et al. |
| 7,297,102 | B2 | 11/2007 | Smith et al. |
| 7,322,993 | B2 | 1/2008 | Metzger et al. |
| 7,337,781 | B2 | 3/2008 | Vassallo |
| 7,360,432 | B2 | 4/2008 | Lehtonen |
| 7,360,542 | B2 | 4/2008 | Nelson et al. |
| 7,367,340 | B2 | 5/2008 | Nelson et al. |
| 7,401,611 | B2 | 7/2008 | Conrad et al. |
| 7,442,389 | B2 | 10/2008 | Quelle et al. |
| 7,601,164 | B2 | 10/2009 | Wu |
| 7,669,603 | B2 | 3/2010 | Knudson et al. |
| 7,806,908 | B2 | 10/2010 | Ruff |
| 7,850,894 | B2 | 12/2010 | Lindh, Sr. et al. |
| 7,857,829 | B2 | 12/2010 | Kaplan et al. |
| 7,888,119 | B2 | 2/2011 | Sugaya et al. |
| 8,142,422 | B2 | 3/2012 | Makower et al. |
| 8,413,661 | B2 | 4/2013 | Rousseau et al. |
| 8,632,488 | B2 * | 1/2014 | Rousseau .................. 604/9 |
| 2001/0037133 | A1 | 11/2001 | Knudson et al. |
| 2002/0144685 | A1 | 10/2002 | Ivanovich |
| 2003/0004579 | A1 | 1/2003 | Rousseau et al. |
| 2003/0034312 | A1 | 2/2003 | Unger et al. |
| 2003/0149445 | A1 | 8/2003 | Knudson et al. |
| 2003/0149447 | A1 | 8/2003 | Morency et al. |
| 2003/0149488 | A1 | 8/2003 | Metzger et al. |
| 2003/0176875 | A1 | 9/2003 | Anderson et al. |
| 2004/0020492 | A1 | 2/2004 | Dubrul et al. |
| 2004/0020498 | A1 | 2/2004 | Knudson et al. |
| 2004/0028676 | A1 | 2/2004 | Klein et al. |
| 2004/0044366 | A1 | 3/2004 | Bonutti et al. |
| 2004/0102796 | A1 | 5/2004 | Hill et al. |
| 2004/0139975 | A1 | 7/2004 | Nelson et al. |
| 2004/0144395 | A1 | 7/2004 | Evans et al. |
| 2004/0147811 | A1 | 7/2004 | Diederich et al. |
| 2004/0149290 | A1 | 8/2004 | Nelson et al. |
| 2004/0153127 | A1 | 8/2004 | Gordon et al. |
| 2004/0231678 | A1 | 11/2004 | Fierro |
| 2005/0038472 | A1 | 2/2005 | Furst |
| 2005/0082452 | A1 | 4/2005 | Kirby |
| 2005/0092334 | A1 | 5/2005 | Conrad et al. |
| 2005/0115572 | A1 | 6/2005 | Brooks et al. |
| 2005/0121039 | A1 | 6/2005 | Brooks et al. |
| 2005/0159637 | A9 | 7/2005 | Nelson et al. |
| 2005/0165352 | A1 | 7/2005 | Henry et al. |
| 2005/0199248 | A1 | 9/2005 | Pflueger et al. |
| 2005/0203576 | A1 | 9/2005 | Sulamanidze et al. |
| 2005/0251255 | A1 | 11/2005 | Metzger et al. |
| 2005/0267321 | A1 | 12/2005 | Shadduck |
| 2005/0267531 | A1 | 12/2005 | Ruff et al. |
| 2005/0267532 | A1 | 12/2005 | Wu |
| 2005/0267571 | A1 | 12/2005 | Spence et al. |
| 2005/0279365 | A1 | 12/2005 | Armijo et al. |
| 2006/0005843 | A9 | 1/2006 | Nelson et al. |
| 2006/0079935 | A1 | 4/2006 | Kolster |
| 2006/0083767 | A1 | 4/2006 | Deusch et al. |
| 2006/0093644 | A1 | 5/2006 | Quelle et al. |
| 2006/0150986 | A1 | 7/2006 | Roue et al. |
| 2006/0185673 | A1 | 8/2006 | Critzer et al. |
| 2006/0206197 | A1 | 9/2006 | Morsi |
| 2006/0207608 | A1 | 9/2006 | Hirotsuka et al. |
| 2006/0207612 | A1 | 9/2006 | Jackson et al. |
| 2006/0228391 | A1 | 10/2006 | Seyedin et al. |
| 2006/0241339 | A1 | 10/2006 | Cook et al. |
| 2006/0266369 | A1 | 11/2006 | Atkinson et al. |
| 2006/0289015 | A1 | 12/2006 | Boucher et al. |
| 2007/0000497 | A1 | 1/2007 | Boucher et al. |
| 2007/0005109 | A1 | 1/2007 | Popadiuk et al. |
| 2007/0005110 | A1 | 1/2007 | Collier et al. |
| 2007/0102004 | A1 | 5/2007 | Nelson et al. |
| 2007/0102010 | A1 | 5/2007 | Lemperle et al. |
| 2007/0110788 | A1 | 5/2007 | Hissong et al. |
| 2007/0119463 | A1 | 5/2007 | Nelson et al. |
| 2007/0123908 | A1 | 5/2007 | Sugaya et al. |
| 2007/0142700 | A1 * | 6/2007 | Fogarty et al. .................. 600/40 |
| 2007/0144531 | A1 | 6/2007 | Tomas et al. |
| 2007/0144534 | A1 | 6/2007 | Mery et al. |
| 2007/0144535 | A1 | 6/2007 | Hegde et al. |
| 2007/0190108 | A1 | 8/2007 | Datta et al. |
| 2007/0204866 | A1 | 9/2007 | Conrad et al. |
| 2007/0209665 | A1 | 9/2007 | Gillis et al. |
| 2007/0227545 | A1 | 10/2007 | Conrad et al. |
| 2007/0233276 | A1 | 10/2007 | Conrad et al. |
| 2007/0246052 | A1 | 10/2007 | Hegde et al. |
| 2007/0256693 | A1 | 11/2007 | Paraschac et al. |
| 2007/0257395 | A1 | 11/2007 | Lindh et al. |
| 2007/0261701 | A1 | 11/2007 | Sanders |
| 2007/0267027 | A1 | 11/2007 | Nelson et al. |
| 2007/0270631 | A1 | 11/2007 | Nelson et al. |
| 2007/0272257 | A1 | 11/2007 | Nelson et al. |
| 2007/0288057 | A1 | 12/2007 | Kuhnel |

(56) References Cited

U.S. PATENT DOCUMENTS

| | | |
|---|---|---|
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Weadock |
| 2010/0037901 A1 | 2/2010 | Rousseau et al. |
| 2010/0080791 A1 | 4/2010 | Rousseau et al. |
| 2010/0106246 A1 | 4/2010 | Rousseau |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1* | 6/2010 | Puisais .................. 424/78.37 |
| 2010/0163056 A1 | 7/2010 | Tschopp et al. |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2011/0245850 A1 | 10/2011 | van der Burg et al. |
| 2012/0123449 A1 | 5/2012 | Schaller et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 | 9/2011 |
| DE | 10245076 | 4/2004 |
| EP | 2145587 | 1/2010 |
| EP | 2386252 A1 | 11/2011 |
| EP | 2517633 | 10/2012 |
| FR | 2651113 | 3/1991 |
| JP | 2001-145646 | 5/2001 |
| JP | 03265621 | 9/2003 |
| JP | 2003265621 | 9/2003 |
| JP | 2009006090 | 6/2007 |
| JP | 2009-6090 A | 1/2009 |
| RU | 2005447 | 1/1994 |
| SU | 927236 | 5/1982 |
| SU | 1697792 | 12/1991 |
| WO | 9713465 | 4/1997 |
| WO | 9900058 | 1/1999 |
| WO | 0066050 | 11/2000 |
| WO | 0121107 | 3/2001 |
| WO | 03096928 | 11/2003 |
| WO | 2004016196 | 2/2004 |
| WO | 2004020492 | 3/2004 |
| WO | 2004021869 | 3/2004 |
| WO | 2004021870 | 3/2004 |
| WO | 2004060311 | 7/2004 |
| WO | 2004084709 | 10/2004 |
| WO | 2004103196 | 12/2004 |
| WO | 2005046554 | 5/2005 |
| WO | WO 2005051292 A2 | 6/2005 |
| WO | 2005082452 | 9/2005 |
| WO | 2005122954 | 12/2005 |
| WO | 2006012188 | 2/2006 |
| WO | 2006072571 | 7/2006 |
| WO | 2006108145 | 10/2006 |
| WO | 2007056583 | 5/2007 |
| WO | 2007075394 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2008118913 | 10/2008 |
| WO | 2009023256 | 2/2009 |
| WO | 2009036094 | 3/2009 |
| WO | 2010019376 | 2/2010 |
| WO | 2010035303 | 4/2010 |
| WO | WO 2010065341 A1 | 6/2010 |
| WO | 2012004758 | 1/2012 |
| WO | 2012041205 | 4/2012 |
| WO | 2012064902 | 5/2012 |
| WO | 2012170468 | 12/2012 |

OTHER PUBLICATIONS

Harries et al., "The Surgical treatment of snoring", Journal of Laryngology and Otology, pp. 1105-1106 (1996).

Wassmuth et al., "Cautery-assisted palatal stiffening operation for the treatment of obstructive sleep apnea syndrome", Otolaryngology—Head and Neck Surgery, vol. 123 (1), pp. 55-60 (2000).

The Pillar Palatal Implant System, Restore Medical, Inc., www.restoremedical.com, 2 pages (2008).

Repose Genioglossus Advancement, INFLUENT Medical, www.influ-ent.com, 1 page (2008).

Cole et al., "Snoring: A Review and a Reassessment", J. of Otolaryngology, pp. 303-306 (1995).

Huang et al., "Biomechanics of snoring", Endeavour, vol. 19(3): pp. 96-100 (1995).

Pang, Kenny et al., "Tongue Suspension Suture in Obstructive Sleep Apnea", Operative Techniques in Otolaryngology, vol. 17, No. 4, Dec. 2006, pp. 252-256.

Schwab et al., "Upper airway and soft tissue changes induced by CPAP in normal subject", Am. J. Respit. Crit. Care Med., vol. 154, No. 4, Oct. 1996, pp. 1106-1116.

Schwartz et al., "Effects of electrical stimulation to the soft palate on snoring and obstructive sleep apnea", J. Prosthetic Dentistry, pp. 273-281 (1986).

Shamsuzzaman et al., "Obstructive Sleep Apnea; Implications for Cardiac and Vascular Disease", JAMA vol. 290 (14); pp. 1906-1914.

Teles et al., "Use of Palatal Lift Prosthesis on Patient Submitted to Maxillectomy: A Case Report", Applied Cancer Res. 2005, vol. 25(3), pp. 151-154.

The Advance System, Aspire Medical, Inc. www.aspiremedical.com, 3 pp (2008).

Vicente et al., "Tongue-Base Suspension in Conjunction with Uvulopapatopharyngoplasty for Treatement of Severe Obstructive Sleep Apnea: Long-term Follow-Up Results", The Laryngoscope, vol. 115(7), pp. 1223-1227 (2006).

Wiltfang et al., "First results on daytime submandibular electrostimulation of suprahyoidal muscles to prevent night-time hypopharyngeal collapse in obstructive sleep apnea syndrom", Intl J. of Oral & Maxillofacial Surgery, pp. 21-25 (1999).

Copy of Notification of Transmittal of the International Search Report and the Written Opinion of the International Search Authority

(56) References Cited

OTHER PUBLICATIONS or the Declaration mailed on Feb. 3, 2010; PCT/US2009/051921; International Filing Date: Jul. 28, 2009.
Copy of Notification of Transmittal of the International Search Report and the Written Opinion of the International Search Authority or the Declaration mailed on May 25, 2010; PCT/US2010/023152; International Filing Date: Apr. 2, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Apr. 29, 2010 for International Patent Application No. PCT/US2009/065293.
International Search Report dated May 25, 2010 for International Patent Application No. PCT/US2010/025778.
Cole et al., "Snoring: A Review and a Reassessment", J. of Otolaryngology, vol. 24, No. 5, 1995, pp. 303-306.
Medtronic AIRvance System for Obstructive Sleep Apnea, http://www.medtronic.com/for-healthcare-professionals/products-therapies/ear-nose-throat/sleep-disordered-breathing-products/airvance-system-for-obstructive-sleep-apnea/index.htm, Oct. 9, 2013, 3 pages.
International Search Report for International Application No. PCT/US2013/043238, dated Oct. 2, 2013, 7 pages.
Database WPI Week 198312, Thomson Scientific, London, GB; AN 1983-D9513K XP002693421, -& SU 927 236 A1 (Petrozazodsk Univ) May 15, 1982 abstract (see figures 7 & 8).
Schleef et al., "Cytokine Activation of Vascular Endothelium, Effects on Tissue-Type 1 Plasminogen Activator Inhibitor" the J. of Biological Chem., vol. 263, No. 12, pp. 5797-5803 (1988).
International Search Report dated Dec. 29, 2009 for International Patent Application No. PCT/US2009/061455.
International Search Report dated Jan. 21, 2010 for International Patent Application No. PCT/US2009/052110.
International Search Report dated May 25, 2010 for International Patent Application No. PCT/US2010/023152.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
International Search Report dated Apr. 9, 2013 for International Patent Application No. PCT/US2012/061569.
International Search Report dated Apr. 2, 2013 for International Patent Application No. PCT/US2012/067708.
Written Opinion dated Nov. 27, 2012 for International Patent Application No. PCT/US2012/056577.

\* cited by examiner

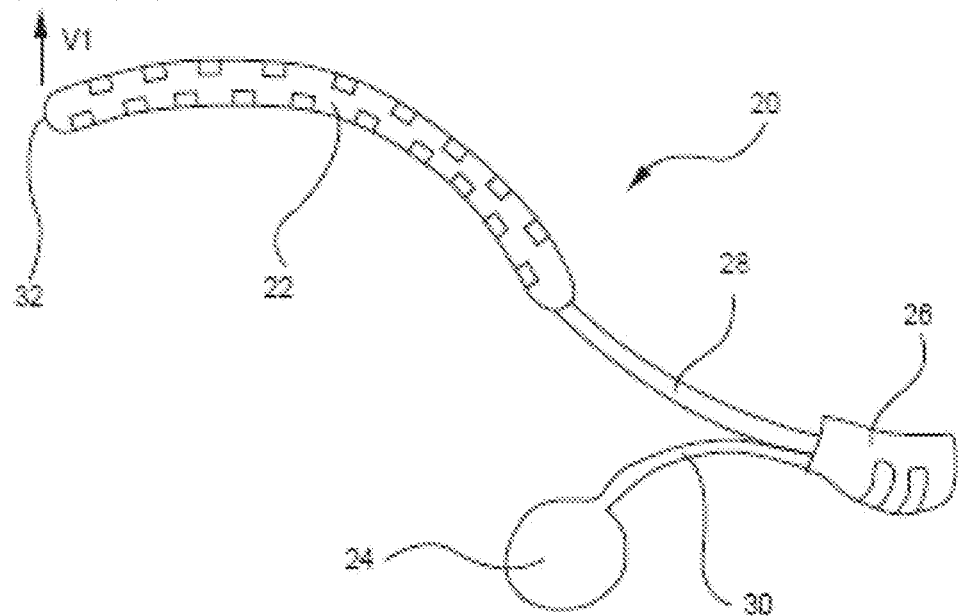
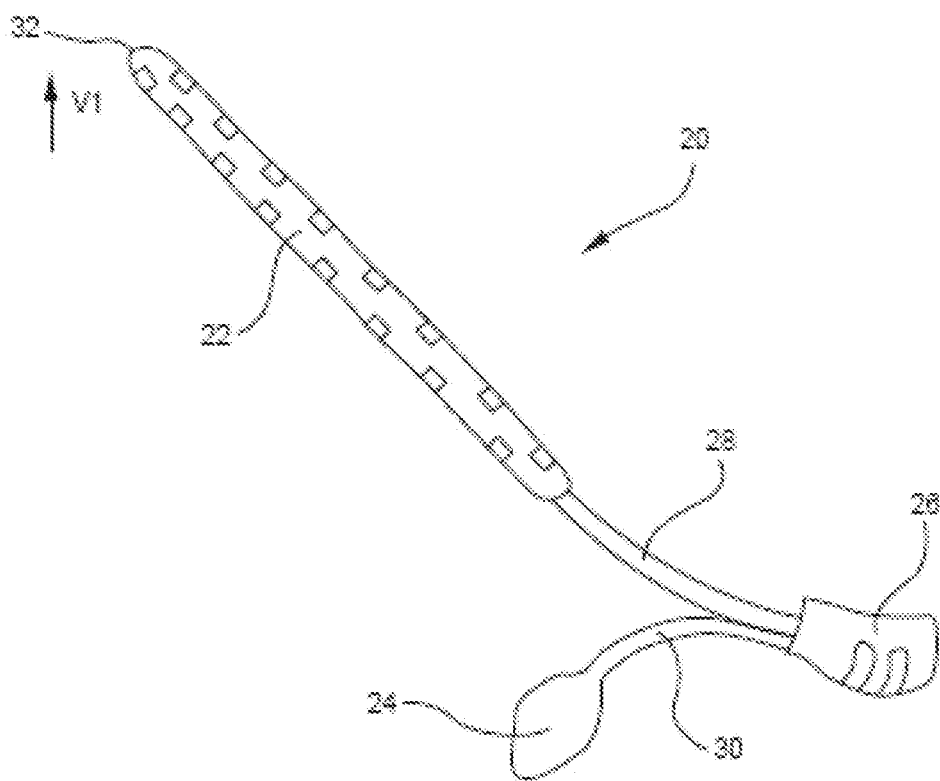

FLUID FILLED IMPLANTS FOR TREATING OBSTRUCTIVE SLEEP APNEA

BACKGROUND OF THE INVENTION

1. Field of the Invention

The present invention generally relates to treating sleep disorders, and more specifically relates to implants, implant systems, devices and methods for treating patients suffering from obstructive sleep apnea.

2. Description of the Related Art

Obstructive sleep apnea (OSA) is caused by a blockage of the airway, which usually occurs when the soft tissue in the throat collapses and closes during sleep. The blockage can occur in a portion of the pharyngeal lumen and may include obstructions formed by the collapse of the tongue against the posterior wall of the pharynx, the collapse of the lateral pharyngeal walls, and the combined collapse of the tongue with impingement of the soft palate, particularly the posterior portion of the soft palate including the uvula. During each apnea event, the brain briefly arouses the sufferer in order to initiate the resumption of breathing. This type of sleep, however, is extremely fragmented and of poor quality.

According to the National Institutes of Health, OSA affects more than twelve million Americans. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. Use of these devices have had mixed results because they require patient adherence to a strict regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal for stiffening the palate.

Surgical procedures such as those mentioned above continue to have problems. Specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Another surgical procedure for treating OSA uses several braided PET cylinders that are implanted in tissue to make the tissues of the tongue or uvula more rigid and less prone to deflection. The Pillar™ Palatal Implant System sold by Restore Medical of St. Paul, Minn. consists of cylindrical-shaped elements of braided polyester filaments that are implanted in the soft palate for reducing the incidence of airway obstructions in patients suffering from mild to moderate OSA. Use of the Pillar device may result in adverse side effects, including extrusion of the cylindrical-shaped elements, infection, and patient discomfort.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" to the tongue, causing device failure and requiring subsequent removal.

Another effort for treating OSA involves creating an auxiliary airway for bypassing the clogged portion of the main airway. In one embodiment of commonly assigned U.S. patent application Ser. No. 12/182,402, filed Jul. 30, 2008, the disclosure of which is hereby incorporated by reference herein, an auxiliary airway is formed by implanting an elongated conduit beneath a pharyngeal wall of the pharynx. The elongated conduit has a proximal end in communication with a first region of the pharynx, a distal end in communication with a second region of the pharynx, and an intermediate section extending beneath the pharyngeal wall for bypassing an oropharynx region of the pharynx.

Magnets have also been used for treating OSA. For example, in one embodiment of commonly assigned U.S. patent application Ser. No. 12/183,955, filed Jul. 31, 2008, the disclosure of which is hereby incorporated by reference herein, a magnetic implant includes a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets. The magnetic implant disclosed in one or more embodiments of the '955 application does not have a hard stop so as to avoid the "cheese-cutter" effect observed when using implants having a hard stop.

In spite of the above advances, there remains a need for additional systems, devices and methods for treating OSA through minimally invasive approaches that provide long term results, that encourage patient compliance, and that minimize patient discomfort.

SUMMARY OF THE INVENTION

In one embodiment of the present invention, an implant for treating obstructive sleep apnea includes a first chamber implantable within the soft tissue of an oropharyngeal airway, such as within a tongue, and a second chamber in communication with the first chamber. The implant also desirably includes a fluid transfer assembly in communication with both the first and second chambers for selectively transferring fluid between the first and second chambers for modifying the rigidity of the first chamber. In one embodiment, the first chamber is flexible and the second chamber includes a fluid reservoir containing a fluid such as a liquid or a gas. In one embodiment, the first chamber is preferably non-expandable, or undergoes limited expansion, so that the rigidity, flexibility and/or shape of the first chamber changes as the fluid pressure increases within the first chamber. In one embodiment, rigidity, flexibility and/or shape of the implant may be changed with minimal or no change to the volume of the implant. In one embodiment, the implant may be used for selectively supporting tissue, such as to treat obstructive sleep apnea, fecal incontinence, etc.

In one embodiment, the first chamber is desirably implantable in the soft tissue of the oropharyngeal airway so as to treat symptoms associated with obstructive sleep apnea. In one embodiment, the first chamber affects the airway of a patient such as by changing the firmness and/or shape of the soft tissue of the oropharyngeal airway so as to maintain the airway open during sleep, thereby minimizing the occurrence of obstructive sleep apnea episodes.

In one embodiment, the first chamber is implantable in a tongue of a patient. The first chamber may also be implantable within a soft palate of a patient, and/or within a pharyngeal wall. In certain preferred embodiments, more than one implant may be implantable in the tongue, the soft palate and/or the pharyngeal wall of a patient. For example, two or more of the first chambers may be implantable in the tongue, the soft palate, or the pharyngeal wall. In one embodiment, one or more of the first chambers may be implantable in a tongue, and one or more of the first chambers may be implantable in another body part such as the soft palate or pharyngeal wall.

The implants disclosed herein may be placed within any one of a wide range of angles relative to an anterior-posterior axis, a vertical axis, a transverse axis, or a horizontal axis of a patient. In one embodiment, the implant(s) may extend laterally relative to the anterior-posterior axis. In one embodiment, the implant(s) may extend in a direction that is parallel with the anterior-posterior axis. In yet another embodiment, the implant(s) may be placed at an angle that lies between the transverse axis and the anterior-posterior axis position. The implants may also be placed along the vertical axis of a patient, the horizontal axis of a patient, or at any angle between the vertical and horizontal axes. The angle that is selected is preferably chosen to maximize therapeutic benefit for a patient.

In one embodiment, the second chamber and the fluid transfer assembly are implanted at a location within the body that is remote from the first chamber. In one embodiment, the second chamber of the implant and the fluid transfer assembly of the implant are implantable within an inframandibular region of a patient. The fluid reservoir and the fluid transfer assembly may be placed subcutaneously within the neck or chest region remote from the location of the flexible, first chamber. The implanted fluid transfer assembly, such as a pump and/or a valve assembly, is desirably engageable by a patient for selectively transferring fluid from the second chamber to the first chamber so as to modify the rigidity, flexibility and/or shape of the first chamber. In one embodiment, a patient uses his or her tactile senses to feel for the fluid transfer assembly beneath the skin and then manipulates the fluid transfer assembly to physically transfer fluid between the fluid reservoir and the first chamber.

In one embodiment, the implant desirably includes a fluid that is disposable within the first and second chambers of the implant. The fluid may include a liquid or a gas that is selectively transferred back and forth between the first and second chambers for modifying the rigidity, flexibility and/or shape of the first chamber.

In one embodiment, the flexible chamber may be produced with an undulating or corrugated tubular structure to facilitate curvilinear deformation of the device in the unstressed condition. In one embodiment, the fluid is passable through the interstices of a corrugated tubular structure to enable the flexible chamber to be readily transformed to rigid state while requiring the use of only a minimum quantity of fluid.

In one embodiment, an implant for treating obstructive sleep apnea includes a flexible chamber, a fluid reservoir in fluid communication with the flexible chamber, and a fluid transfer assembly in communication with the fluid reservoir and the flexible chamber for transferring fluid between the fluid reservoir and the flexible chamber. As the fluid is transferred from the fluid reservoir to the flexible chamber, the rigidity of the flexible chamber is modified. In one embodiment, as fluid is introduced into the flexible chamber, the flexible chamber becomes more rigid. When it is desirable to reduce the rigidity of the flexible chamber (e.g. when a patient awakes), a patient may engage the fluid transfer assembly so as to transfer the fluid from the flexible chamber back to the fluid reservoir. As the fluid is withdrawn from the flexible chamber and returned to the fluid reservoir, the rigidity of the flexible chamber is preferably reduced.

In one embodiment, the implant includes a flexible conduit that interconnects and provides fluid communication between the flexible chamber and the fluid reservoir. The flexible conduit may also provide fluid communication between the fluid transfer assembly and both the flexible chamber and the fluid reservoir. In one embodiment, the implant may include two or more flexible conduits for forming the fluid communication links described above.

In one embodiment, the flexible chamber is configured as a straight device that can be deformed into a curvilinear geometry during installation. The deformed flexible chamber changes into the preferred shape as the fluid is transferred from the fluid reservoir to the flexible chamber. In one embodiment, the flexible chamber is flexible and is deformed into a slightly curved configuration before the fluid is transferred between the fluid reservoir and the flexible chamber. The flexible chamber may be in the flexible configuration when the patient is awake. Before the patient goes to bed for the night, the fluid is transferred to the flexible chamber so that the flexible chamber becomes more rigid and resumes an un-deformed configuration.

In one embodiment, a surgical implant for treating obstructive sleep apnea includes a flexible chamber implantable within the soft tissue of an oropharyngeal airway of a patient. The implant desirably includes a fluid reservoir implantable within an infra-mandibular region of the patient and that is in fluid communication with the flexible chamber. In one embodiment, the surgical implant desirably includes a fluid transfer assembly implantable within the patient and being in communication with the fluid reservoir and the flexible chamber. The fluid transfer assembly is desirably engageable by the patient for selectively transferring fluid between the fluid reservoir and the flexible chamber for modifying the rigidity, flexibility and/or shape of the flexible chamber. In one embodiment, the flexible chamber, the fluid reservoir and the fluid transfer assembly may be made of biocompatible materials.

In one embodiment, the flexible chamber becomes more rigid as the fluid is transferred from the fluid reservoir to the flexible chamber, and becomes less rigid as the fluid is transferred back from the flexible chamber to the fluid reservoir. In one embodiment, the flexible chamber desirably changes shape as the fluid is transferred between the fluid reservoir and the flexible chamber.

In one embodiment, a device for the treatment of obstructive sleep apnea includes an implant that is placed within the tongue and that is in fluid communication with a fluid reservoir located within the infra-mandibular region or other soft tissue location. The implant preferably includes a pump and/or valve assembly for transferring fluid from the reservoir to the tongue implant to provide increased pressure and rigidity of the implant thereby forcing an alteration in the flexibility of the implant. The increased rigidity causes the shape of the tongue to be altered to provide an increased dimension in the vertical axis of the tongue, which causes a reduction in the anterior-posterior thickness of the tongue, and which tends to open the oral-pharyngeal region of the pharynx. The fluid transfer assembly is desirably integral to the implant and is embedded within the tissue of the patient so that the patient is capable of pressurizing the device prior to sleep to maintain the shape of the tongue shape when the genioglossus muscle relaxes during sleep. Upon waking, the patient is able to activate the fluid transfer assembly (e.g. a valve) to reduce the pressure within the tongue implant to increase the flexibility of the tongue for regular activities of speech, swallowing, etc. One or more of the implants may be placed within the tissues of the pharyngeal wall and/or the soft palate to provide support to or favorably alter the shape of these tissues to facilitate maintaining an open airway for breathing.

In one embodiment, the flexible, first chamber is desirably formed from either two pieces of film material, such as polymer films, or one piece of film material that is folded onto itself and that is applied to the end of a fluid transfer tube. The fluid transfer tube is desirably supplied with a hole in the sidewall of the tube that is in communication with an inner lumen extending along the longitudinal axis of the tube. In one embodiment, an inner layer of film material is desirably shorter than an outer layer of film material. The inner layer is preferably intended to only be fixated about the end of the tube that is distal to the hole in the side of the tube. The inner and outer layers are preferably wrapped around the end of the tube, with the inner layer being bonded to the distal end of the transfer tube. The outer layer is desirably bonded to the proximal side of the sidewall hole in the transfer tube. In one embodiment, the perimeters of the two inner and outer layers are preferably bonded together to form a sealed chamber between the two layers of film and the free edge is bonded to form a circular cylindrical shape. The formation of the dual wall cylinder enables a reduction in the fluid volume required to enable pressurization of the cylinder as only the compartment between the two layers is filled.

In one embodiment, the flexible, first chamber may be formed as a standard unitary compartment, similar to a typical balloon or pouch. In this embodiment, a greater volume of fluid is required to be transferred into the chamber to enable the cylinder to become more rigid.

In one embodiment, the first chamber has a surface adapted to promote tissue in-growth. The tissue in-growth promoting surface is desirably selected from a group of outer surfaces including a textured surface, a porous surface, a braided surface, a mesh surface, a fleece surface, and a coating such as hydroxyapatite for inducing bone or tissue in-growth. In one embodiment, the first chamber is made of any of the well-known flexible, durable, biocompatible materials. In one embodiment, the first chamber may be made of any of the well-known biocompatible polymers and biocompatible elastomeric materials. In one embodiment, the first chamber may be made of silicone, latex, polyurethane, nylon, or polyester, or combinations thereof.

Although the present invention is not limited by any particular theory of operation, it is believed that the fluid filled implant of the present application provides a number of benefits over prior art devices. First, the fluid filled implant may be removed from a patient if efficacious results are not obtained. Second, the fluid filled implant desirably affects the target tissue when it is pressurized at night or during sleep, thereby minimizing the chances of affecting speech or swallowing. In one embodiment, a patient may control the rigidity and shape of the fluid filled implant without requiring external devices or appliances. In addition, the fluid filled implant of the present invention preferably changes the shape of the tongue, or other tissues in the upper airway, without requiring a hard anchoring point thereby minimizing the chance of the implant tearing out or pulling through the tissue. In one embodiment, the fluid filled implant desirably includes a thin walled pressure chamber that is designed to produce the volume of fluid required to provide significant stiffening of the implant and to reduce the volume of fluid required to be removed from the implant for returning the implant to a flexible condition.

In one embodiment, when the flexible chamber is pressurized by a fluid, the implant regains a straightened, cylindrical, or other three dimensional shape so as to provide support and shape for a relaxed tongue or soft tissue. Posterior displacement of the tongue is minimized and the resultant airway is enlarged. In one embodiment, a patient may selectively control the rigidity of the implant. When a patient is ready for sleep, the rigidity compartment is pressurized by activation of a pump through the skin. In the case of manual pumping, a bulb is squeezed. In one embodiment, the pump is remotely operated and may be activated through the skin through the use of magnetic coupling or electrical field energy. Upon waking, a patient may depress the valve so as to enable fluid transfer to the second compartment for reducing the pressure within the pressurized compartment of the implant. Once the flexible chamber is in the non-pressurized condition, the tongue is able to move freely and is unaffected by the presence of the implant. Thus, the implant only affects movement of the tongue during sleep and does not affect a patients' ability to speak or swallow when the patient in awake.

In one embodiment, the implant includes a pressurized cylinder. In the event of forceful swallowing during sleep, the implant may deform temporarily to allow swallowing. After the muscular activity related to swallowing subsides, the implant preferably returns to the preferred shaped so as to provide support and re-shaping of the relaxed tongue or tissue of the upper airway.

In one preferred embodiment, a fluid filled implant may be utilized to provide favorable support and re-shaping of an airway upon demand by a patient. In one embodiment, an implant is fabricated from flexible film materials so patients are not aware that the implant is in place. In one embodiment, a pump or valve may be included in-line within two layers of film that have been thermo-formed into a bladder shape on one end and bonded together on the opposing end to provide a "unitary" type construction without requiring extra bonding seams or joints.

These and other preferred embodiments of the present invention will be described in more detail below.

BRIEF DESCRIPTION OF THE DRAWING

FIG. 5A shows an implant for treating obstructive sleep apnea including a flexible chamber, a fluid reservoir and a fluid transfer assembly, in accordance with one embodiment of the present invention.

FIG. 5B shows the implant of FIG. 5A after fluid has been transferred from the fluid reservoir to the flexible chamber, in accordance with one embodiment of the present invention.

DETAILED DESCRIPTION

Figure 1:
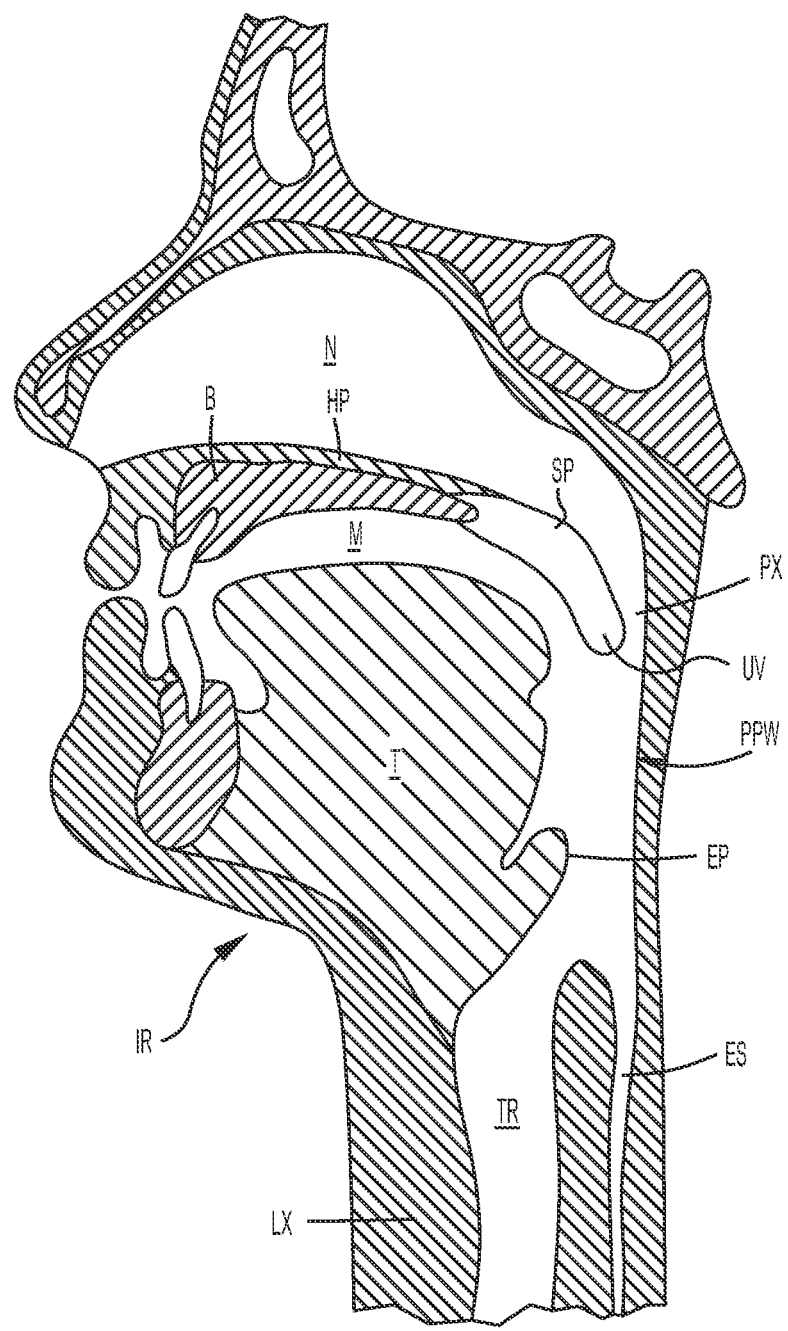
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP including the uvula UV at the posterior end thereof, the mouth M, the tongue T, the trachea TR, the epiglottis EP, the esophagus ES, and the posterior pharyngeal wall PPW.

Figure 2:
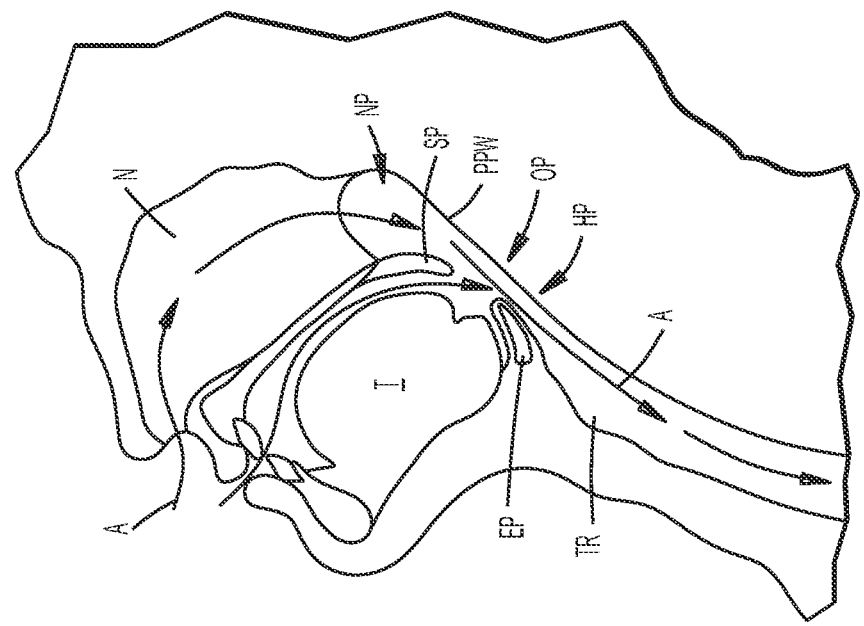
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW. The midline posterior end of the soft palate is referred to as the uvula, which is the soft tissue that extends downward from the soft palate over the back of the tongue.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent, which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Figure 3:
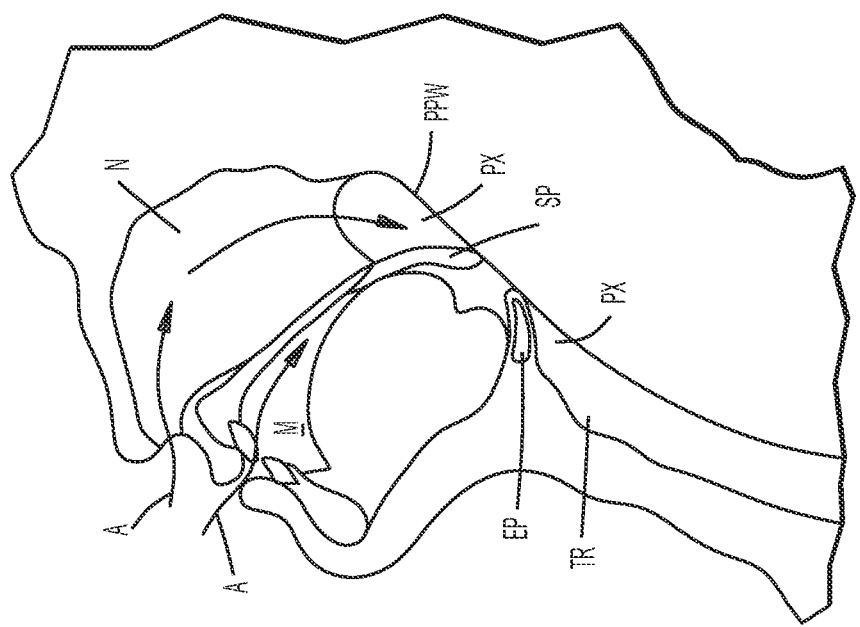
FIG. 3 shows a cross-sectional view of the nasal cavity and the pharynx of a human during an obstructive sleep apnea episode.

Referring to FIG. 3, without normal muscle tone to keep their shape and to keep them in place either alone or as a group, the posterior surface of the tongue T, the epiglottis EP, and the soft palate SP tend to easily collapse to block the airway A.

Figure 4:
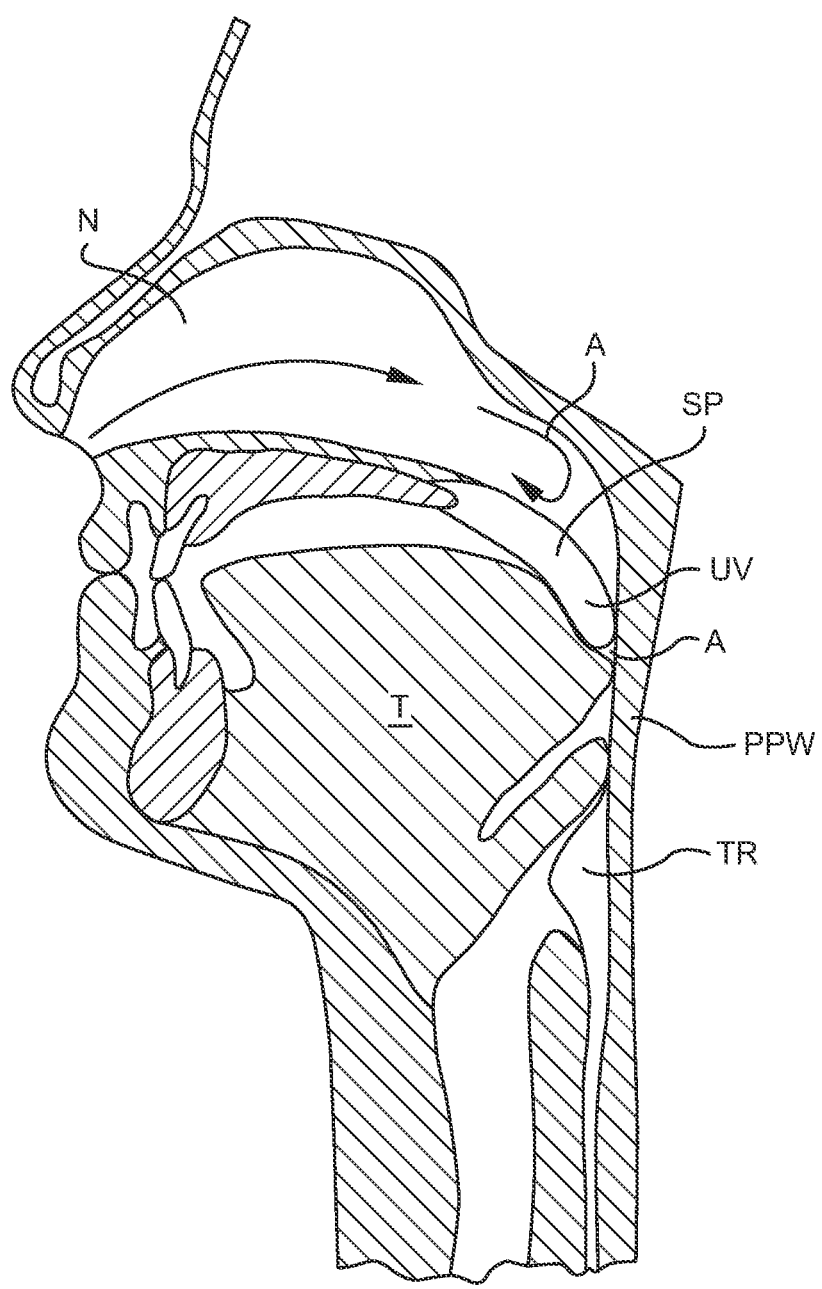
FIG. 4 shows another cross-sectional view of the nasal cavity and the pharynx of a human during an obstructive sleep apnea episode.

Referring to FIG. 4, during sleep, the posterior end of the tongue T may block the airway A between the nasal passages N and the upper end of the trachea TR. The soft palate SP may also relax and the uvula UV slide between the back of the tongue T and the posterior pharyngeal wall PPW. In one embodiment, the present invention provides an implant that firms and/or changes the shape of the soft tissue of the upper airway so that it does not move into the position shown in FIG. 4. The implant also desirably provides support to the tongue T so that it does not sag in a posterior direction against the posterior pharyngeal wall, as shown in FIG. 4.

Referring to FIG. 5A, in one preferred embodiment of the present invention, an implant 20 for treating obstructive sleep apnea includes a first chamber 22, a second chamber 24 and a fluid transfer assembly 26. The first and second chambers 22, 24 are preferably in communication with one another via the fluid transfer assembly 26. In one embodiment, the first chamber 22 is normally flexible and becomes more rigid when fluid is introduced into the first chamber 22. In one embodiment, the second chamber 24 is preferably expandable and desirably includes a reservoir adapted to store fluid.

In one embodiment, the implant 20 preferably includes a first conduit 28 extending between the fluid reservoir 22 and the fluid transfer assembly 26. The first conduit 28 preferably provides communication between the fluid reservoir 22 and the fluid transfer assembly 26 so that fluid may be passed therebetween. The implant 20 also preferably includes a second conduit 30 that desirably extends between the fluid transfer assembly 26 and the second chamber 24.

Referring to FIG. 5B, in one preferred embodiment, fluid may be extracted from the fluid reservoir 24 and introduced into the first chamber 22 using the fluid transfer assembly 26. In one embodiment, the fluid transfer assembly 26 may be compressed and released so as to draw fluid from the fluid reservoir 24, transfer the fluid through the first and second conduits 28, and introduce the fluid into the first chamber 22. Referring to FIGS. 5A and 5B, as the fluid is transferred from the second chamber 24 to the first chamber 22, the first chamber 22 becomes more rigid so as to transform the first chamber 22 from the flexible state shown in FIG. 5A to the straighter, more rigid state shown in FIG. 5B. As the first chamber 22 becomes straighter and more rigid, a distal tip 32 of the first chamber 22 moves upwardly in a vertical direction designated $V_1$.

In one embodiment, it may be desirable to return the implant 20 from the rigid state shown in FIG. 5B to the flexible state shown in FIG. 5A. This may be accomplished by operating the fluid transfer assembly 26, such as a pump and/or a valve, for removing the fluid from the first chamber 22, and transferring the fluid to the second chamber 24 or fluid reservoir via the first and second conduits 28, 30. In one embodiment, the fluid transfer assembly 26 is operated to remove the fluid from the first chamber 22. The fluid then passes through the first conduit 28, through the fluid transfer assembly 26, through the second conduit 30, and into the fluid reservoir 24. Once the fluid has been returned to the fluid reservoir 24, the first chamber 22 assumes the flexible state or configuration shown in FIG. 5A. The first chamber 22 will remain in the flexible state of FIG. 5A until a patient desires to increase the rigidity of the first chamber. The patient may repeatedly and selectively change the configuration of the first chamber 22 by either introducing fluid into the first chamber 22 or removing fluid from the first chamber 22.

Figure 6A:
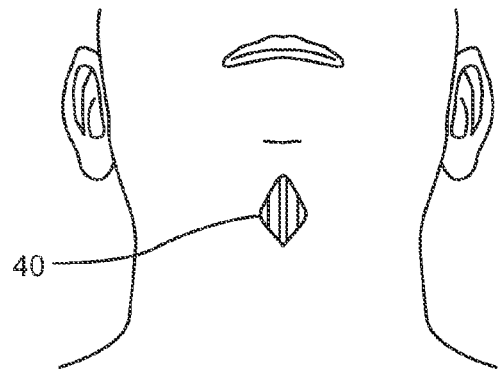
FIGS. 6A-6C show a method of implanting the implant show in FIGS. 5A and 5B in a tongue, in accordance with one embodiment of the present invention.

Referring to FIG. 6A, in one embodiment, the implant shown and described above in FIGS. 5A and 5B may be implanted in a patient's tongue by forming an incision 40 within the infra-mandibular region and within the tongue.

Figure 6B:
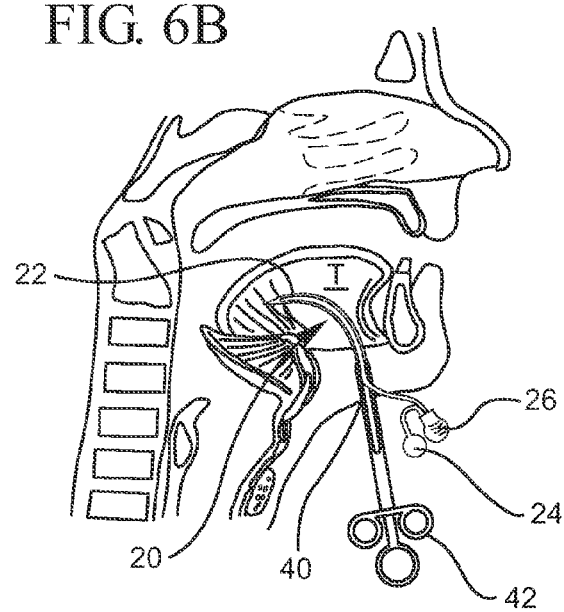
Figure 6C:
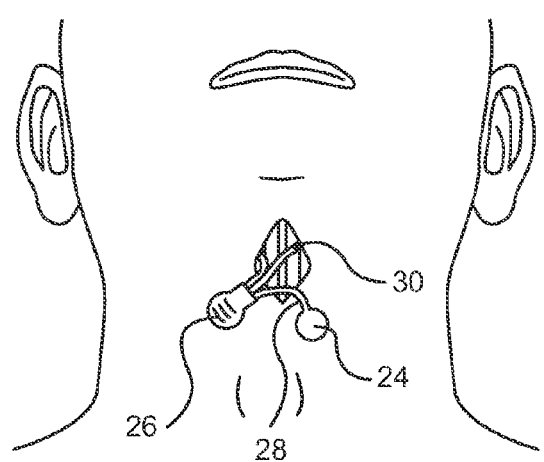

Referring to FIG. 6B, in one embodiment, an insertion tool 42 is desirably used for passing the implant 20 through the incision 40 and into the tongue T. The incisions may be formed and the device implanted in the tongue using well known surgical techniques and tools. As shown in FIGS. 6B and 6C, the first chamber 22 of the implant 20 is preferably implanted within the tongue. The first chamber 22 is desirably not pressurized upon implantation and remains conformable to the shape of the tongue and/or the surrounding tissue. The fluid reservoir 24 and the fluid transfer assembly 26 of the implant are desirably implanted below the mandible.

Figure 7A:
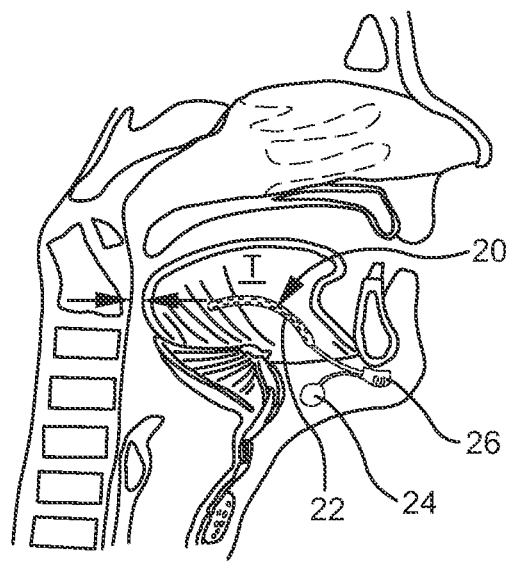
FIG. 7A shows a cross-sectional view of a human head with the implant in the flexible state shown in FIG. 5A, in accordance with one embodiment of the present invention.
Figure 7B:
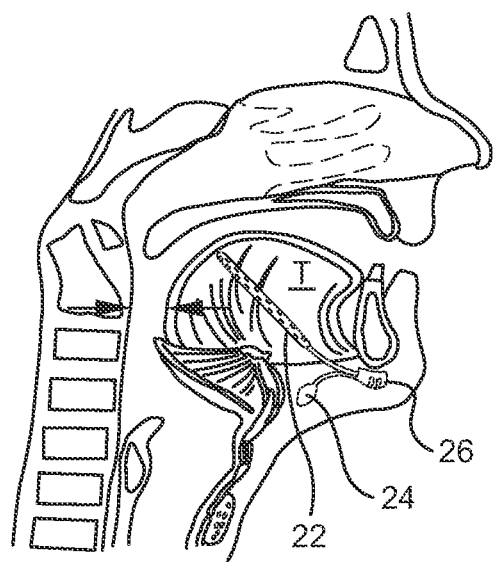
FIG. 7B shows a cross-sectional view of a human head with the implant in the rigid state shown in FIG. 5B, in accordance with one embodiment of the present invention.

FIG. 7A shows the implant 20 after the first chamber 22 has been implanted in the tongue T. In one embodiment, after the implantation procedure is complete, the first chamber 22 is positioned within the tongue T and the reservoir 24 and fluid transfer assembly 26 are positioned in the infra-mandibular region of the patient. Referring to FIG. 7B, the fluid transfer assembly 26 may be operated for transferring fluid from the fluid reservoir 24 to the first chamber 22. As the first chamber 22 is pressurized by the fluid, first chamber becomes rigid as it assumes the straightened, cylindrical shape shown in FIG. 7B to provide support and shape to the tongue T. In response, posterior displacement of the tongue T is minimized and the resultant airway is enlarged, as shown by the tips of the arrows present in FIG. 7B. In one embodiment, the implant 20 is preferably adapted to be controlled by a patient. When the patient is ready for sleep, the patient engages the fluid transfer assembly 26 through the skin for introducing fluid into the first chamber 22 and transforming the second chamber from the flexible state of FIG. 7A to the more rigid state of FIG. 7B. In one embodiment, a patient may use manual pumping by squeezing a bulb. In another embodiment, the fluid transfer assembly 26 may be remotely operated through the skin using magnetic coupling or electric field energy. The patient will then sleep with the implant 20 in the configuration shown in FIG. 7B. Upon wakening, a patient may engage the fluid transfer assembly 26 so as to remove the fluid from the first chamber 22 for reducing the pressure within the first chamber 22. In the flexible or reduced pressure condition shown in FIG. 7A, the tongue T is preferably able to move freely and is unaffected by the presence of the implant 20. Thus, in one embodiment, the only affect is on the tongue T during sleep and the implant and it is not noticeable when the patient is awake. As a result, the implant 20 will not affect speech or swallowing. In addition, because the implant is a pressurized cylinder fabricated from flexible materials, in the event that a patient has forceful swallowing during sleep, the implant may deform temporarily to allow swallowing. After the muscular activity associated with swallowing has ceased, the implant 20 resumes the preferred shape shown in FIG. 7B to support and shape a relaxed tongue.

Figure 8A:
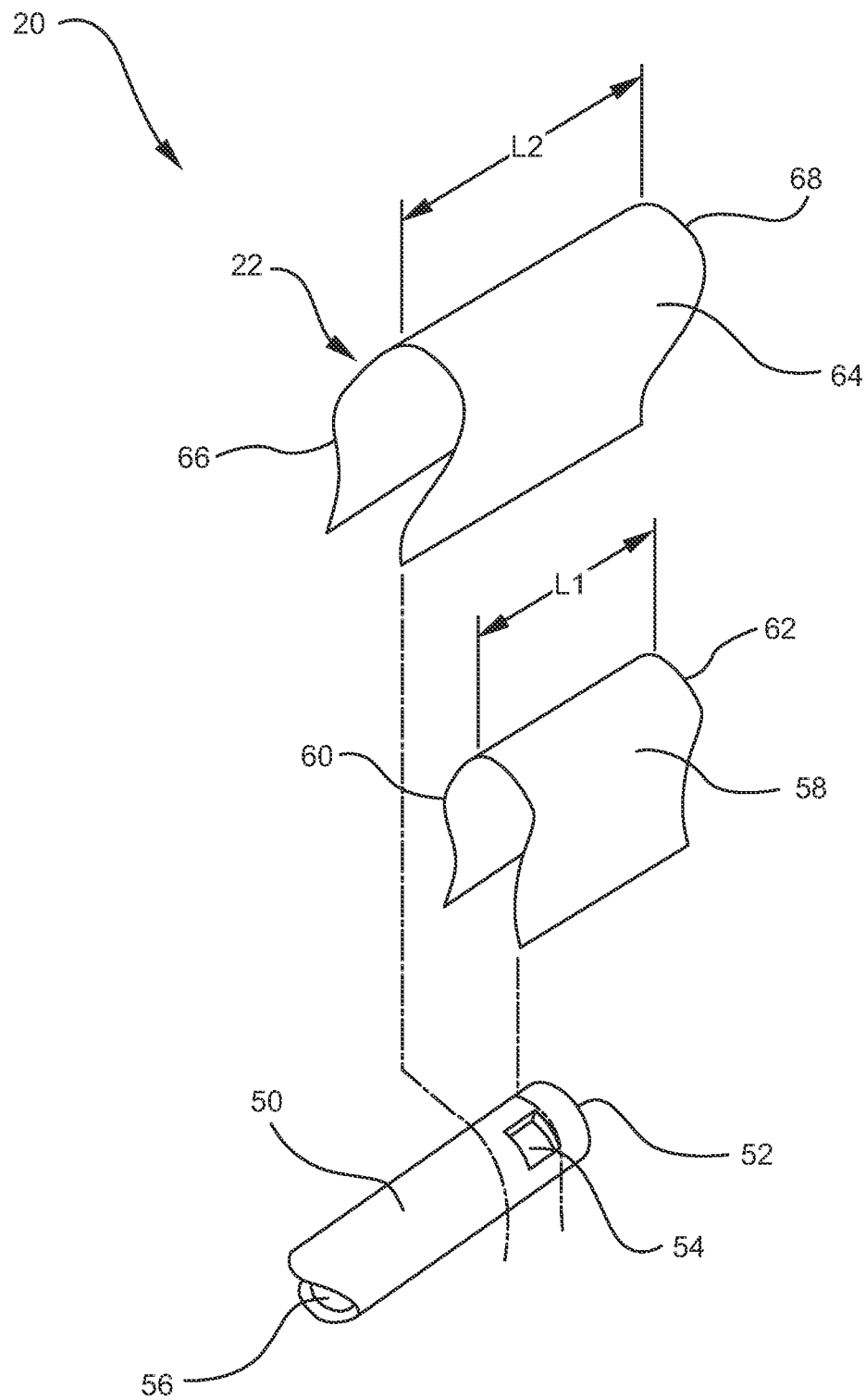
FIG. 8A shows an exploded view of an implant for treating obstructive sleep apnea, in accordance with one embodiment of the present invention.
Figure 8B:
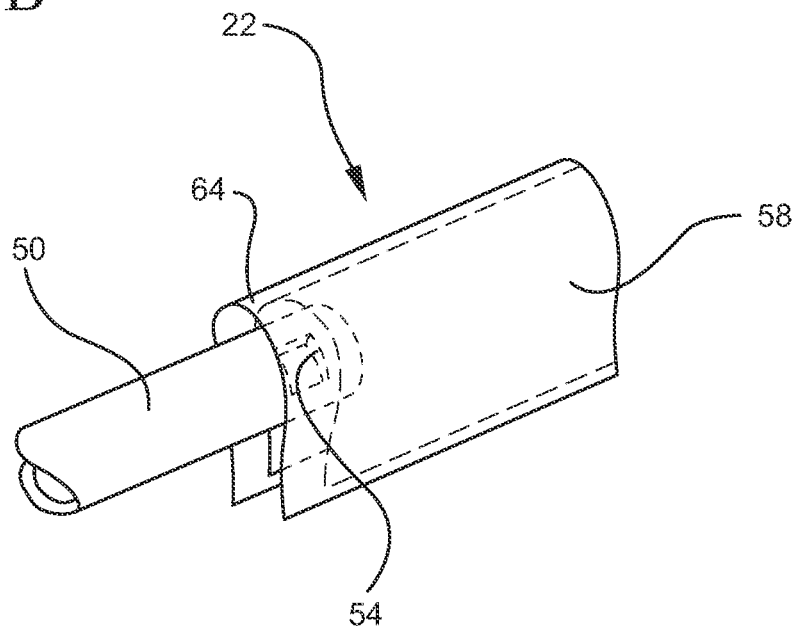
FIG. 8B shows a partially assembled view of the implant for treating obstructive sleep apnea shown in FIG. 8A.
Figure 8C:
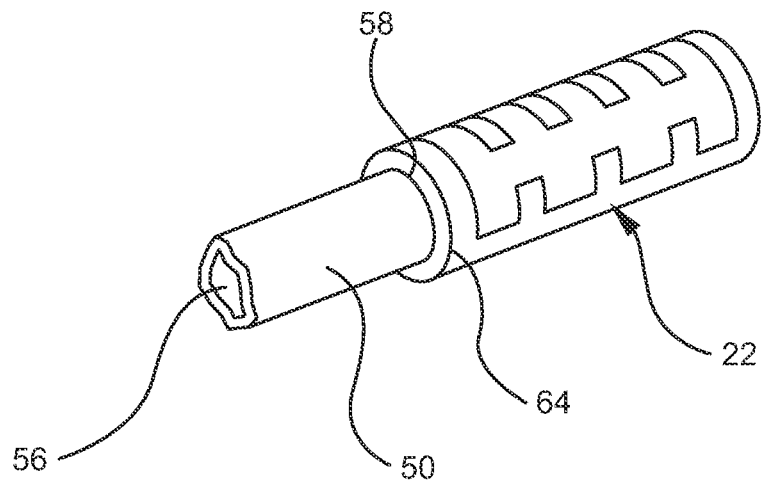
FIG. 8C shows the implant of FIGS. 8A and 8B after assembly, in accordance with one embodiment of the present invention.

A broad description of the implant for treating obstructive sleep apnea has been described above. FIGS. 8A-8C show an implant, in accordance with one particular preferred embodiment of the present invention. Referring to FIG. 8A, in one embodiment, the distal end of the implant 20 preferably includes a transfer tube 50 having a distal end 52 and a radial opening 54 formed in the outer surface of the tube 50. The radial opening 54 may be located adjacent the distal end 52 of the tube 50. As fluid is forced toward the distal end 52 of the transfer tube 50, the fluid passes through a central conduit 56 and out of the radial opening 54. When it is desired to transform the implant from the rigid state to a flexible state, the fluid is removed through the radial opening 54 and the elongated conduit 56.

The distal end of the implant preferably has the first chamber 22 including an inner layer 58 that is secured over the outer surface of the transfer tube 50. The inner layer 58 preferably has a proximal edge 60 and a distal edge 62. The proximal edge 60 is preferably secured to an outer surface of the tube 50 between a distal end of the radial opening 54 and the distal end 58 of the transfer tube 50. The distal edge 62 of the inner layer 58 preferably extends beyond the distal end 52 of the transfer tube 50. In one embodiment, the inner layer 58 is preferably wrapped around the outer surface of the transfer tube 50 to form a cylindrical shaped element. The proximal edge 60 is preferably secured to the outer surface of the transfer tube 50 so as to form a fluid-tight seal therewith.

The first chamber 22 also preferably includes an outer layer 64 having a proximal edge 66 and a distal edge 68. The outer layer 64 preferably overlies the inner layer 58. In one embodiment, the proximal edge 66 of the outer layer 64 is preferably attached to the outer surface of the transfer tube at a location that is proximal to the radial opening 54. The outer layer 64 is preferably wrapped around the inner layer 58 and the transfer tube 50 to form a cylindrical-shaped element. The distal edge 68 of the outer layer 64 is preferably secured to the distal edge 62 of the inner layer 58 and forms a fluid-tight seal therewith.

In one embodiment, the inner layer 58 has a length $L_1$ that is preferably shorter than the outer layer 64, which has a length $L_2$. The inner and outer layers are preferably wrapped around the distal end of the transfer tube, with the inner layer being bonded to the distal end of the transfer tube. The outer layer is preferably bonded to the transfer tube 50 proximal to the radial opening 54. The perimeters of the inner and outer layers 58, 64 are preferably bonded together to form a sealed chamber between the inner and outer layers of film and the free edges are bonded to form the cylindrical-shaped device as illustrated in FIG. 8C. The formation of a dual-walled cylindrical-shaped element enables a reduction in the fluid volume required to pressurize the cylinder. In other embodiments, the first chamber may have a corrugated or "honey-combed" interior structure that enables a smaller volume of fluid to be used for transforming the first chamber from a more flexible state to a more rigid state. These preferred designs require less fluid than is required for providing rigidity to a hollow structure such as a balloon or pouch.

Referring to FIG. 8B, in one embodiment, the inner layer 58 and the outer layer 64 are assembled over the distal end of the transfer tube 50. The respective distal edges 62, 68 of the inner and outer layers 58, 64 are preferably secured together to form a fluid-tight seal. The proximal edge 60 of the inner layer 58 is secured to the outer surface of the transfer tube 50 at a location that is distal to the radial opening 54, and the proximal edge 66 of the outer layer 64 is preferably secured to the outer surface of the transfer tube 50 at a location that is proximal to the radial opening 54. The fluid that passes through the radial opening 54 desirably fills the gap between the inner and outer layers 58, 64 for expanding the first chamber 22.

Referring to FIG. 8C, in one embodiment, fluid is forced through the conduit 56 toward the distal end of the transfer tube. As the fluid reaches the distal end of the transfer tube 50, the fluid passes through radial opening 54 (not shown) and fills a space or gap between the inner layer 58 and the outer layer 64. As the fluid pressure increases within the space between the inner and outer layers 58, 64, the first chamber 22 becomes more rigid. The use of the two layer design minimizes the volume of fluid required to provide rigidity to the first chamber so that less fluid is needed to transform the first chamber from a more flexible state to a more rigid state.

In one embodiment, the first chamber 22 may be formed as a standard unitary compartment, similar to a balloon or pouch. In this particular embodiment, a greater volume of fluid may be required to be transferred into the second chamber to enable the first chamber to become rigid.

Figure 9:
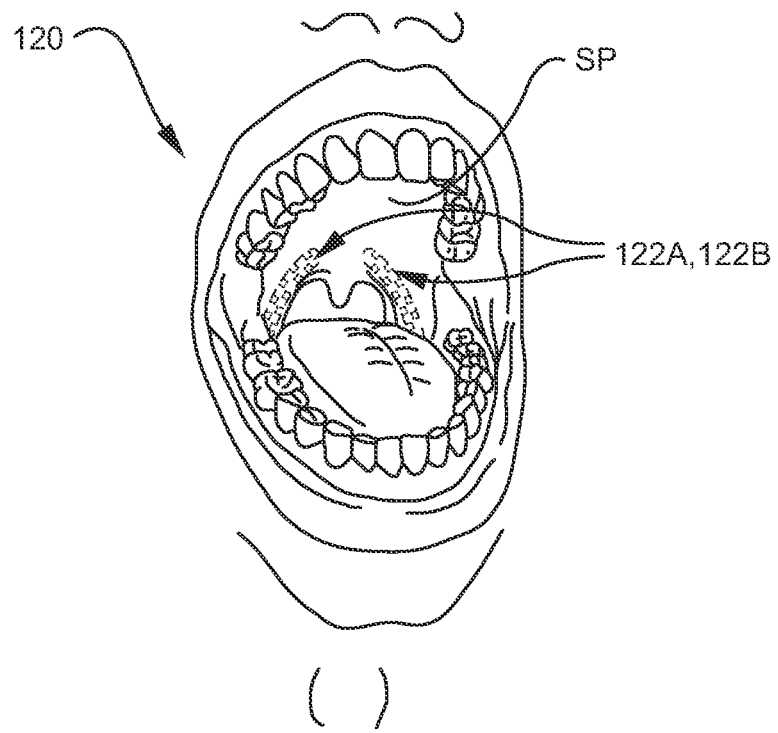
FIG. 9 shows a system for treating obstructive sleep apnea including at least one fluid filled implant disposed in a soft palate of a patient, in accordance with one embodiment of the present invention.

Referring to FIG. 9, in one embodiment, an implant 120 for treating obstructive sleep apnea is positioned within the soft tissues of the palate. In one particular embodiment, the implant includes a first implant and a second implant positioned within the soft palate SP. In the particular embodiment shown in FIG. 9, the first implant preferably includes a first chamber 122A positioned within a soft palate SP, and the second implant preferably includes a first chamber 122B, positioned within the soft palate SP. The fluid pressure within the respective first chambers 122A, 122B may be increased for changing the shape and/or rigidity of the respective first chambers 122A, 122B, which, in turn, changes the shape and/or holds the shape of the soft palate SP. In the embodiment shown in FIG. 9, the fluid transfer assembly and the fluid reservoir elements are placed remotely from the location of the first chambers 122A, 122B.

Figure 10:
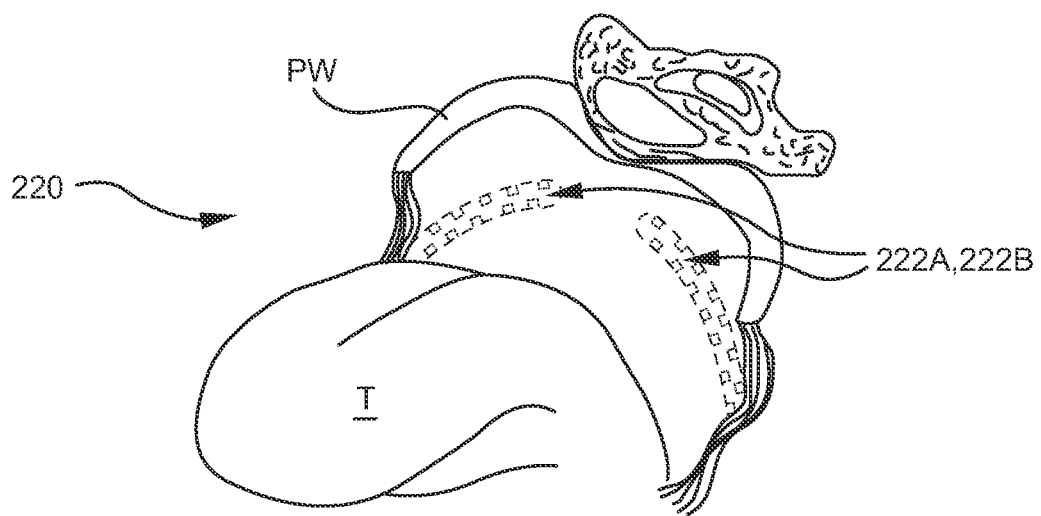
FIG. 10 shows a system for treating obstructive sleep apnea including at least one fluid filled implant disposed in a pharyngeal wall, in accordance with one embodiment of the present invention.

Referring to FIG. 10, in one embodiment, an implant described herein is positioned within the pharyngeal walls PW of a patient. In FIG. 10, the system includes a first implant having a first chamber 222A, and a second implant having a first chamber 222B. The respective first chambers 222A, 222B are implanted in the pharyngeal wall PW. The fluid reservoirs and the fluid transfer assemblies for the implants are preferably placed remotely from the location of the first chambers 222A, 222B.

Figure 11:
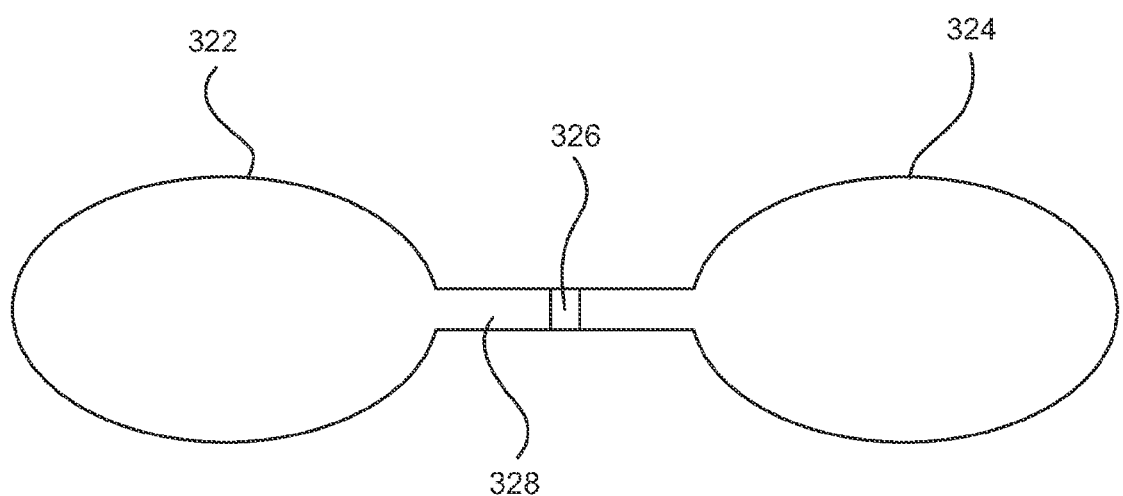
FIG. 11 shows an implant for treating obstructive sleep apnea, in accordance with one embodiment of the present invention.

Referring to FIG. 11, in one embodiment, an implant 320 for treating obstructive sleep apnea includes a flexible chamber 322 desirably implantable within soft tissue of an oropharangyeal airway, and a fluid reservoir 324 preferably implantable within an inframandibular region of a patient. The flexible chamber 322 and the fluid reservoir 324 are desirably in fluid communication with one another via a fluid transfer assembly extending therebetween. The fluid transfer assembly desirably includes a fluid conduit 328 that interconnects the flexible chamber 322 and the fluid reservoir 324. The implant 320 also preferably includes a valve 326, such as a duck-bill valve, that enables fluid to be transferred back and forth between the flexible chamber 322 and the fluid reservoir 324. The valve 326 may be engaged by a patient for transferring fluid, such as saline solution, between the fluid reservoir and the flexible chamber so as to modify the rigidity, flexibility, and/or shape of the flexible chamber. In one embodiment, the implant 320 shown in FIG. 11 is a unitary structure that has a seam located around the outer perimeter of the implant. In one embodiment, the flexible chamber 322, the fluid reservoir 324, and the fluid conduit 328 may comprise two flexible films that are joined together around the perimeter of the films. The valve 326 may be disposed between the two joined flexible films for controlling the flow of fluid between the flexible chamber and the fluid reservoir.

Although the present invention is not limited by any particular theory of operation, it is believed that the implants for treating obstructive sleep apnea disclosed herein may be utilized to provide favorable support and reshaping of the airway upon demand from a patient. Since the implant devices of the present invention are fabricated from flexible film materials, the implant devices are not noticeable when the patient is awake. In certain preferred embodiments of the present invention, the implant is formed of flexible films. In one embodiment, the fluid transfer assembly may be included in-line with two layers of film that have been thermo-formed into a bladder shape on one end and bonded together on the opposing end to provide a "unitary" type construction without requiring extra bonding, seams or joints.

In one embodiment, the implant may have an outer surface that encourages tissue in-growth so as to stabilize the implant within the tissue and so as to minimize the opportunity for tissue erosion. The outer surface modification may be achieved by texturizing the outer surface, making the implant porous through the addition of holes (e.g. drilled or pierced holes), encapsulating the implant with a braided, surgical mesh, or fleece type material, and/or coating the implant with bone growth stimulating agents such as hydroxyapatite.

The present invention provides a number of advantages over prior art methods and devices used for treating obstructive sleep apnea syndrome and hypopnea. First, the methods, systems and devices disclosed herein provide for simple surgical procedures that are minimally invasive. Typically, the methods, systems and devices disclosed herein may be utilized during an outpatient procedure. In addition, the methods, systems and devices disclosed herein provide both immediate and long term results for treating obstructive sleep apnea syndrome and hypopnea. Moreover, the methods, systems and devices disclosed herein do not require a significant level of patient compliance.

In addition, the present invention does not anchor the tongue to a fixed hard structure, such as the mandible. Thus, the present invention is significantly less likely to affect swallowing or speech, thereby providing a great improvement over prior art devices, systems and methods. The present invention also preferably uses materials having long-term biocompatibility.

Although various embodiments disclosed herein relate to use in humans, it is contemplated that the present invention may be used in all mammals, and in all animals having air passages. Moreover, the methods, systems and devices disclosed herein may incorporate any materials that are biocompatible, as well as any solutions or components that minimize rejection, enhance tissue ingrowth, enhance the formation of mucosal layers, and improve acceptance of the device by a body after the device has been implanted.

The present application may incorporate one or more of the features disclosed in commonly assigned U.S. patent application Ser. No. 12/182,402, filed Jul. 30, 2008; Ser. No. 12/183,955, filed Jul. 31, 2008; Ser. No. 12/257,563, filed Oct. 24, 2008; Ser. No. 12/261,102, filed Oct. 30, 2008; and Ser. No. 12/325,350, filed Dec. 1, 2008; and U.S. Patent Appln. Pub. Nos. 2007/0005109 and 2007/0005110, the disclosures of which are hereby incorporated by reference herein.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. An implant for treating obstructive sleep apnea comprising:
   a first chamber implantable within soft tissue of an oropharyngeal airway;
   a second chamber in fluid communication with said first chamber;
   a fluid transfer assembly in fluid communication with said first and second chambers for transferring fluid between said first and second chambers for modifying the rigidity of said first chamber, wherein said fluid transfer assembly adapted to be is squeezed for drawing fluid from said second chamber and introducing said drawn fluid into said first chamber, wherein said first chamber comprises a flexible chamber and said second chamber comprises an expandable fluid reservoir, and wherein said first chamber becomes more rigid and said expandable fluid reservoir shrinks as said fluid transfer assembly draws said fluid from said second chamber and introduces said fluid into said first chamber, and wherein said first chamber becomes less rigid and said second expandable fluid reservoir expands as said fluid transfer assembly removes said fluid from said first chamber and returns said fluid back to said second chamber.

2. The implant as claimed in claim 1, wherein said first chamber, said second chamber, and said fluid transfer assembly comprise a unitary structure, and wherein said implant does not have a fluid inlet.

3. The implant as claimed in claim 1, wherein said first chamber is implantable in a tongue.

4. The implant as claimed in claim 1, wherein said first chamber is implantable within the soft tissue at any selected angle relative to an anterior-posterior, lateral, vertical, or horizontal axis of a patient.

5. The implant as claimed in claim 1, wherein said first chamber is implantable within a soft palate.

6. The implant as claimed in claim 1, wherein said first chamber is implantable within a pharyngeal wall.

7. The implant as claimed in claim 1, wherein said second chamber and said fluid transfer assembly are implantable within an inframandibular region of a patient.

8. The implant as claimed in claim 1, wherein said fluid comprises a liquid or a gas.

9. An implant for treating obstructive sleep apnea comprising:
   a flexible chamber;
   a fluid reservoir in fluid communication with said flexible chamber;
   a fluid transfer assembly in fluid communication with said fluid reservoir and said flexible chamber for transferring fluid therebetween so as to selectively modify the rigidity of said flexible chamber, wherein said fluid transfer assembly adapted to be is squeezed for drawing fluid from said fluid reservoir and introducing said drawn fluid into said flexible chamber, wherein said flexible chamber becomes more rigid as said fluid transfer assembly draws said fluid from said fluid reservoir and introduces said fluid into said flexible chamber, wherein said flexible chamber becomes less rigid and the volume of said fluid in said fluid reservoir expands as said fluid transfer assembly removes said fluid from said flexible chamber and returns said fluid to said fluid reservoir, wherein said flexible chamber is implantable within soft tissue of an oropharyngeal airway of a patient, and wherein said fluid reservoir and said fluid transfer assembly are implantable within the inframandibular region of the patient.

10. The implant as claimed in claim 9, wherein said fluid transfer assembly is compressed and released for drawing said fluid from said fluid reservoir and introducing said drawn fluid into said flexible chamber, and wherein the volume of said fluid in said fluid reservoir is reduced as said fluid is transferred to said flexible chamber.

11. The implant as claimed in claim 9, further comprising a flexible conduit extending between said flexible chamber and said fluid reservoir for transferring fluid therebetween.

12. The implant as claimed in claim 9, wherein said flexible chamber becomes more rigid as said fluid is transferred from said fluid reservoir to said flexible chamber and less rigid as said fluid is transferred back from said flexible chamber to said fluid reservoir.

13. The implant as claimed in claim 9, wherein said flexible chamber is adapted to change shape as said fluid is transferred between said fluid reservoir and said flexible chamber.

14. The implant as claimed in claim 9, wherein said flexible chamber is implantable in the soft tissue of an upper airway, a midline of a sagittal plane of a tongue, a soft palate, or a pharyngeal wall.

15. A surgical implant for treating obstructive sleep apnea comprising:
    a flexible chamber implantable within the soft tissue of an oropharyngeal airway of a patient;
    a fluid reservoir implantable within an inframandibular region of the patient and being in fluid communication with said flexible chamber;
    a fluid transfer assembly implantable within the patient and being in fluid communication with said fluid reservoir and said flexible chamber, wherein said fluid transfer assembly is engageable by the patient for transferring fluid between said fluid reservoir and said flexible chamber for modifying the rigidity of said flexible chamber, and wherein said fluid transfer assembly is compressed and released for drawing fluid from said fluid reservoir and transferring said drawn fluid to said flexible chamber.

16. The surgical implant as claimed in claim 15, wherein said fluid transfer assembly comprises:
    a conduit extending between said flexible chamber and said fluid reservoir;
    a valve disposed within said conduit for regulating fluid flow between said flexible chamber and said fluid reservoir.

17. The surgical implant as claimed in claim 16, wherein said valve is adapted to open in response to a positive pressure differential between said fluid in said flexible chamber and said fluid in said fluid reservoir.

18. The surgical implant as claimed in claim 15, wherein said flexible chamber, said fluid reservoir and said fluid transfer assembly comprise biocompatible materials.

19. The surgical implant as claimed in claim 15, wherein said flexible chamber becomes more rigid and the volume of said fluid in said fluid reservoir is reduced as said fluid is transferred from said fluid reservoir to said flexible chamber and said flexible chamber becomes less rigid and the volume of said fluid in said fluid reservoir expands as said fluid is transferred back from said flexible chamber to said fluid reservoir.

20. The surgical implant as claimed in claim 15, wherein said flexible chamber is adapted to change shape as said fluid is transferred between said fluid reservoir and said flexible chamber.

21. The surgical implant as claimed in claim 15, wherein said flexible chamber, said fluid reservoir, and said fluid transfer assembly comprise a unitary structure.

22. An implant for treating obstructive sleep apnea comprising:
    a flexible chamber;
    a fluid reservoir in fluid communication with said flexible chamber;
    a fluid transfer assembly in communication with said fluid reservoir and said flexible chamber for transferring fluid therebetween so as to selectively modify the rigidity of said flexible chamber;
    wherein said flexible chamber is implantable within soft tissue of an oropharyngeal airway of a patient, wherein said fluid reservoir and said fluid transfer assembly are implantable within the inframandibular region of the patient, and wherein said fluid transfer assembly adapted to be is squeezed for drawing fluid from said fluid reservoir and transferring said drawn fluid to said flexible chamber.

23. A surgical implant for treating obstructive sleep apnea comprising:
    a flexible chamber implantable within the soft tissue of an oropharyngeal airway of a patient;
    a fluid reservoir implantable within an inframandibular region of the patient and being in fluid communication with said flexible chamber;
    a fluid transfer assembly implantable within the patient and being in communication with said fluid reservoir and said flexible chamber, wherein said fluid transfer assembly is engageable by the patient for transferring fluid between said fluid reservoir and said flexible chamber for modifying the rigidity of said flexible chamber;
    wherein said flexible chamber is adapted to change shape as said fluid is transferred between said fluid reservoir and said flexible chamber;
    wherein said fluid transfer assembly is adapted to be squeezed for drawing said fluid from said fluid reservoir and transferring said drawn fluid to said flexible chamber.

24. A surgical implant for treating obstructive sleep apnea comprising:
    a flexible chamber implantable within the soft tissue of an oropharyngeal airway of a patient;
    a fluid reservoir implantable within an inframandibular region of the patient and being in fluid communication with said flexible chamber;
    a fluid transfer assembly implantable within the patient and being in communication with said fluid reservoir and said flexible chamber, wherein said fluid transfer assembly is engageable by the patient for transferring fluid between said fluid reservoir and said flexible chamber for modifying the rigidity of said flexible chamber;
    wherein said fluid transfer assembly comprises:
        a conduit extending between said flexible chamber and said fluid reservoir;
        a valve disposed within said conduit for regulating fluid flow between said flexible chamber and said fluid reservoir, wherein said fluid transfer assembly adapted to be is squeezed for drawing said fluid from said fluid reservoir and transferring said drawn fluid to said flexible chamber, and wherein a volume of said fluid in said fluid reservoir is reduced when said fluid is transferred to said flexible chamber and the volume of said fluid in said fluid reservoir expands when said fluid is returned from said flexible chamber back to said fluid reservoir.

* * * * *